United States Patent [19]
Iijima et al.

[11] Patent Number: 5,939,404
[45] Date of Patent: Aug. 17, 1999

[54] CANCER METASTASIS INHIBITOR CONTAINING A *STREPTOCOCCUS AGALACTIAE* IA TYPE OR IB TYPE SURFACE POLYSACCHARIDE AS A MAIN INGREDIENT

[75] Inventors: Shinji Iijima; Katsuhide Miyake; Shin Yamamoto; Yasuko Yoshida; Mitsuo Kawase, all of Nagoya, Japan

[73] Assignee: NGK Insulators, Ltd., Japan

[21] Appl. No.: 08/894,461

[22] PCT Filed: Dec. 27, 1995

[86] PCT No.: PCT/JP95/02735

§ 371 Date: Aug. 19, 1997

§ 102(e) Date: Aug. 19, 1997

[87] PCT Pub. No.: WO97/24130

PCT Pub. Date: Jul. 10, 1997

[51] Int. Cl.$^6$ ............... A61K 31/715; A61K 39/09; C08B 37/00
[52] U.S. Cl. ............ 514/54; 514/23; 536/123.1; 536/123; 424/244.1
[58] Field of Search ............ 424/244.1; 514/54, 514/23; 536/123.1, 123

[56] References Cited

U.S. PATENT DOCUMENTS 4,413,057 11/1983 Carlo et al. .................. 435/101

FOREIGN PATENT DOCUMENTS

| | | |
|---|---|---|
| 57-175123 | 10/1982 | Japan . |
| 57-212122 | 12/1982 | Japan . |
| 6-501383 | 2/1994 | Japan . |
| WO 95/19374 | 7/1995 | WIPO . |

OTHER PUBLICATIONS

Cell Technology: Y. Kawamura et al. "Adhesion between cancer cells and the endothelial cells via sugar chains", vol. 7, pp. 1151–1157, No. 8, Jul. 1993.

*Primary Examiner*—Francisco Prats

[57] ABSTRACT

The present invention relates to the technology for inhibiting the cancer metastasis, and is aimed at the provision of a pharmaceutical composition for effectively inhibiting the metastasis of the cancer. A cancer metastasis inhibitor according to the present invention is characterized by containing a sugar chain separated from a surface of a *Streptococcus agalactiae* Ia type or Ib type as a main ingredient. Since the surface sugar chains of the *Streptococcus agalactiae* Ia type or Ib type have structures similar to surface sugar chains of the cancer cells, the former surface sugar chains adhere to E-selectin appearing in an intravascular endothelial cell, competitively inhibit the adhesion between intravascular endothelial cells and the cancer cells, and effectively prevent of the metastasis of the cancer, when the sugar chains exist in blood of a patient.

3 Claims, 10 Drawing Sheets

Mechanism of metastasis

FIG. 2
Cancer cell surface sugar chain and Streptococcus agalactiae Ia type, Ib type
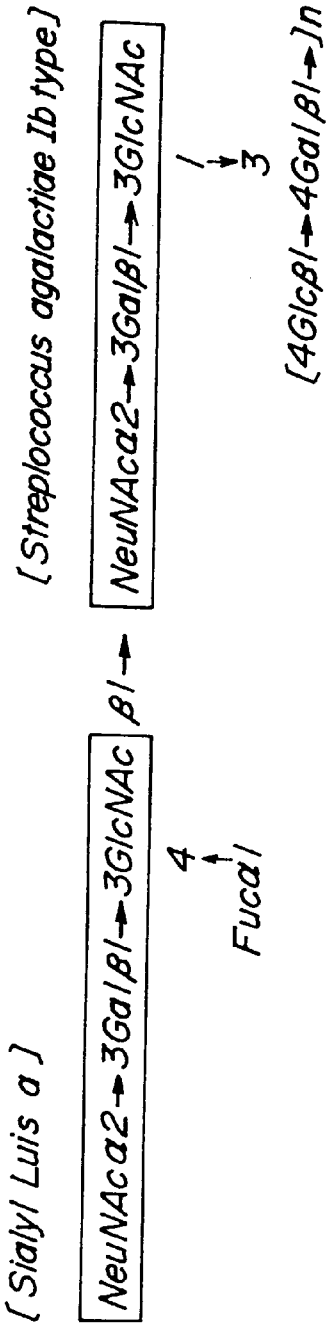
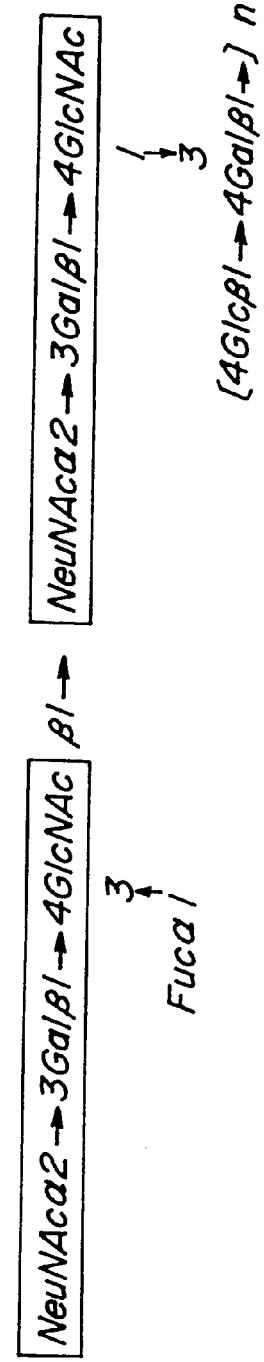

FIG_3

Separation, purification and identification of Streptococcus agalactiae Ia type or Ib type surface sugar chain Adhesion assay

FIG_7
*E-selectin expression appearance in human intravascular endothelial cells*
| | IL-1β Fig. 7(a) + | Fig. 7(c) − |
|---|---|---|
| Human normal intravascular cells | 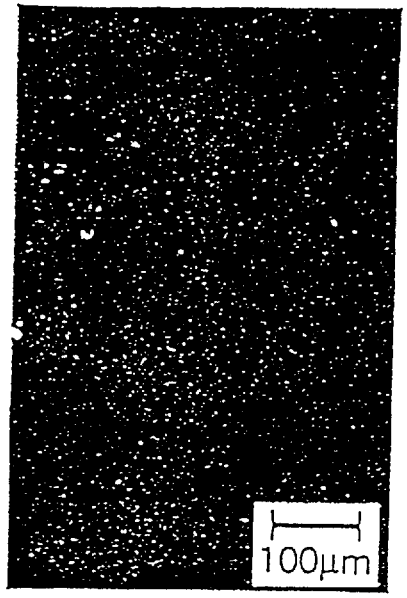 | 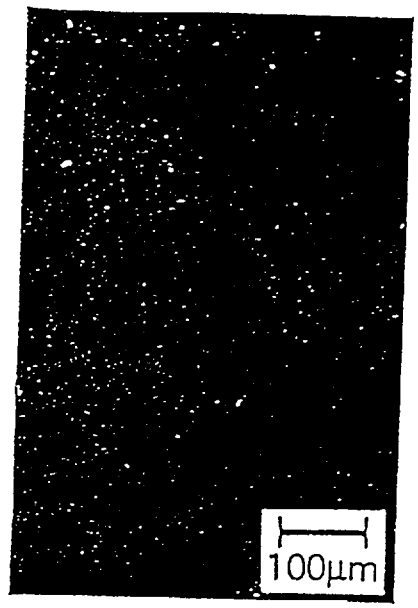 |
| Human intravascular endothelial cells #5-1 | 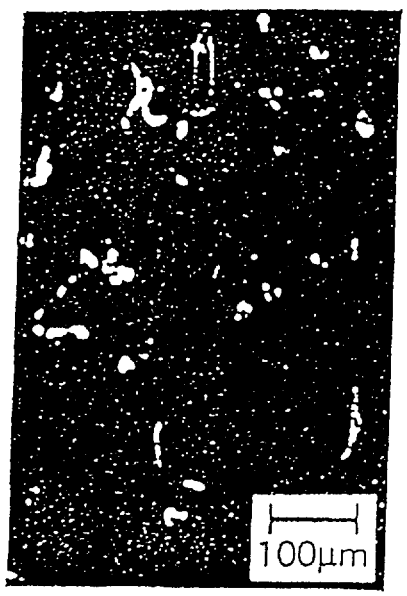 | 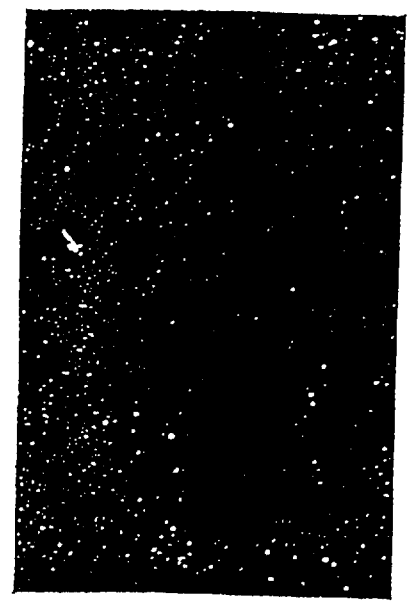 |
| | Fig. 7(b) | Fig. 7(d) |

FIG. 8
Inhibition of adhesion between cancer cells and human intravascular endothelial cells
Fig. 8(a) IL-1β −
Fig. 8(b) IL-1β +
Fig. 8(c) IL-1β + surface sugar chain
200um

FIG. 9
Effect of surface sugar chains from Streptococcus agalactiae on cell adhesion between HL-60 cells and human intravascular endothelial cells
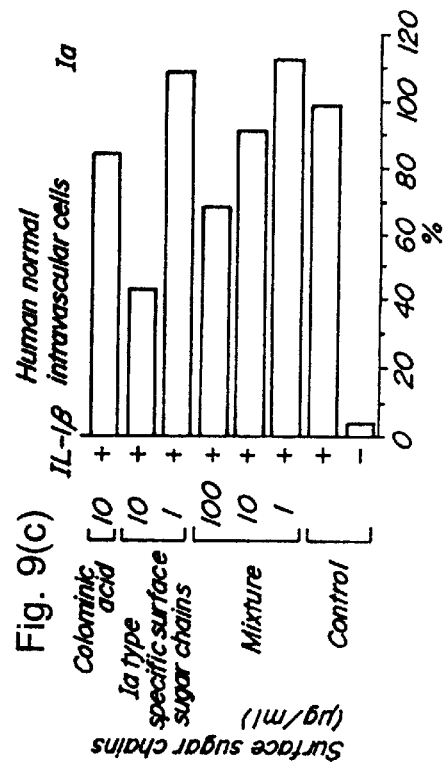
Fig. 9(a)
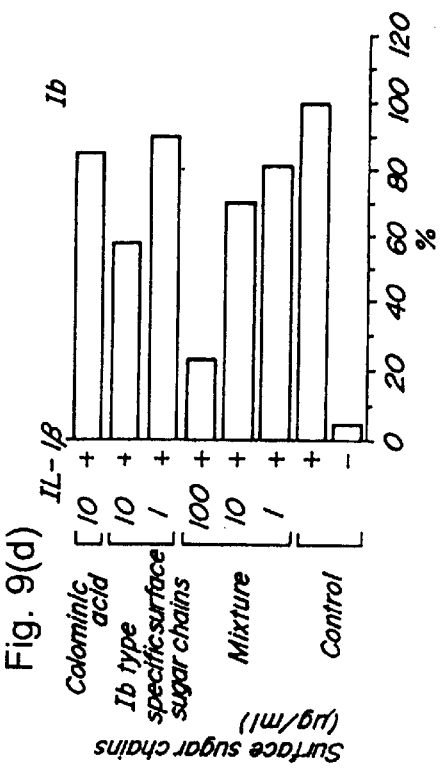
Fig. 9(b)
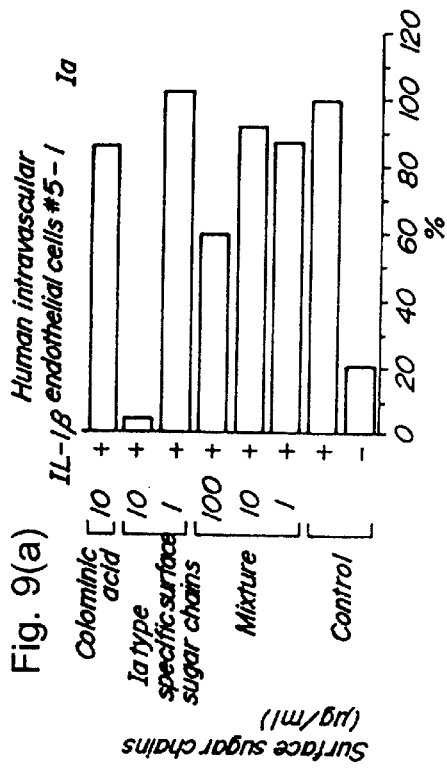
Fig. 9(c)
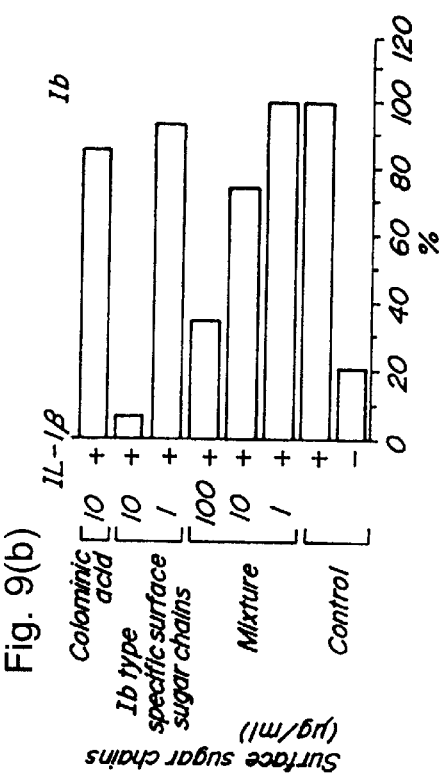
Fig. 9(d)

Effect of surface sugar chains from Streptococcus agalactiae on cell adhesion between Colo201 cells and human intravascular endothelial cells

CANCER METASTASIS INHIBITOR CONTAINING A *STREPTOCOCCUS AGALACTIAE* IA TYPE OR IB TYPE SURFACE POLYSACCHARIDE AS A MAIN INGREDIENT

This application is a 371 of international application number PCT/JP95/02375, filed Dec. 27, 1995.

TECHNICAL FIELD

The present invention relates to a cancer metastasis inhibitor containing a sugar chain separated from the surface of a streptococcus agalactiae Ia type or Ib type surface polysaccharide as a main ingredient.

BACKGROUND TECHNOLOGY

As the cancer therapeutic method, a chemotherapy in which various antitumor agents are administrated, an immunotherapy in which production of an antibody to cancer cells is accelerated, a surgical therapy in which cancer cells are removed or enucleated, radiotherapy in which cancer cells are killed by irradiating radioactive rays upon them, etc. are employed.

However, even if a primary cancer is completely healed, a problem may still exist. That is, the reason why the cancer is a malignant tumor is that the cancer is metastatic, and that persons are often killed with metastatic cancers provoked by metastasis of cancer cells. It cannot be said that a method for suppressing the metastasis of the cancer cells has been established, and it is a present situation that a medicine having a cancer cell metastasis suppressing effect has not yet been made commercially available.

On the other hand, a few or several steps are considered for the metastasis mechanism, and a casual relationship between the cancer metastasis and the sugar chain has been recently discussed in academic meetings. In the metastasis of the cancer cells, cancer cells are first released from a cancer-developed site, and are carried and moved through a human body with blood. E-selectin as one of intercellular adhesive molecules appears on the surface of an intravascular endothelial cell for a certain reason. This E-selectin interacts with free cancer cells moving through the human body with blood, which causes a rolling phenomenon in which the free cancer cells roll on the surfaces of the intravascular endothelial cells and reduce their moving speed in the blood. Consequently, the free cancer cells are adhered to the intravascular endothelial cells through the rolling phenomenon. Then, the cancer cells pass between the intravascular endothelial cells, and enter vascular tissues, so that a new cancer cell nest is formed (See FIG. 1).

In this series of steps, the adhesion between the E-selectin, appearing as one of the intercellular adhesive molecules, on the surface of an intravascular endothelial cell and the sugar chain present at the surfaces of the cancer cells plays a very important role in an initial stage of the adhesion between the cancer cells and the intravascular endothelial cells. As an antibody against the sugar chain at the surface of the cancer cell which sugar chain interacts with the E-selectin, sialic acid-containing complex sugar chains called sialyl $Le^a$ and sialyl $Le^x$ have been identified.

DISCLOSURE OF THE INVENTION

Having noted that the surface sugar chain of a Ia type or Ib type of bacteria called *Streptococcus agalactia* has a structure very similar to that of the sugar chain called sialyl $Le^a$ or sialyl $Le^x$ as the antibody against the sugar chain at the surface of the cancer cell (See FIG. 2), the present inventors have completed the present invention based on an idea that the metastasis of the cancer cells might be prevented by utilizing the surface sugar chain originating from the *Streptococcus agalactia* bacteria Ia type or Ib type. The surface sugar chains originating from the *Streptococcus agalactia* bacteria Ia type and Ib type differ from the antibody against the surface sugar chain of the cancer cell only in that the sialyl $Le^a$ and sialyl $Le^x$ as the antibody against the sugar chains at the surface of the cancer cell have a fucose residue, whereas the surface sugar chains originating from the *Streptococcus agalactia* bacteria Ia type and Ib type have glucose and galactose polymerized as in FIG. 2.

More specifically, the present inventors have noted the surface sugar chains originating from the *Streptococcus agalactia* bacteria Ia type and Ib type, and considered if the adhesion among the above polysaccharides and the cancer cells and the intravascular endothelial cell could be competitively inhibited by utilizing the polysaccharide separated and purified from these bacteria. As a result of strenuous investigations, the present inventors have accomplished the present invention.

That is, the present invention is to provide a cancer metastasis inhibitor for effectively inhibiting the metastasis of the cancer.

The cancer metastasis inhibitor according to the present invention is characterized by being composed mainly of at least any one of the surface sugar chains originating from the *Streptococcus agalactia* bacteria Ia type and Ib type.

Since the surface sugar chains originating from the *Streptococcus agalactia* bacteria Ia type and Ib type used in the present invention have the structures similar to that of the sugar chain at the surface of the cancer cell, such surface sugar chains adhere to E-selectin appearing at the intravascular endothelial cells when the sugar chains exist in blood, so that adhesion between the intravascular endothelial cells and the cancer cells is competitively inhibited to effectively prevent the metastasis of the cancer.

Further, although the polysaccharide outside the *Streptococcus agalactia* bacteria can exhibit cytotoxicity as it is, an oligomer obtained by decomposing the sugar chain at the surface of the above bacteria is used in the present invention. Accordingly, the metastasis of the cancer can be prevented with higher safety.

BRIEF DESCRIPTION OF THE INVENTION

FIG. 2 is a figure for illustrating the structures of the sialyl Lewis $Le^a$, sialyl Lewis $Le^x$ and the sugar chains originating from the surfaces of the *Streptococcus agalactia* bacteria Ia and Ib;

Figure 1:
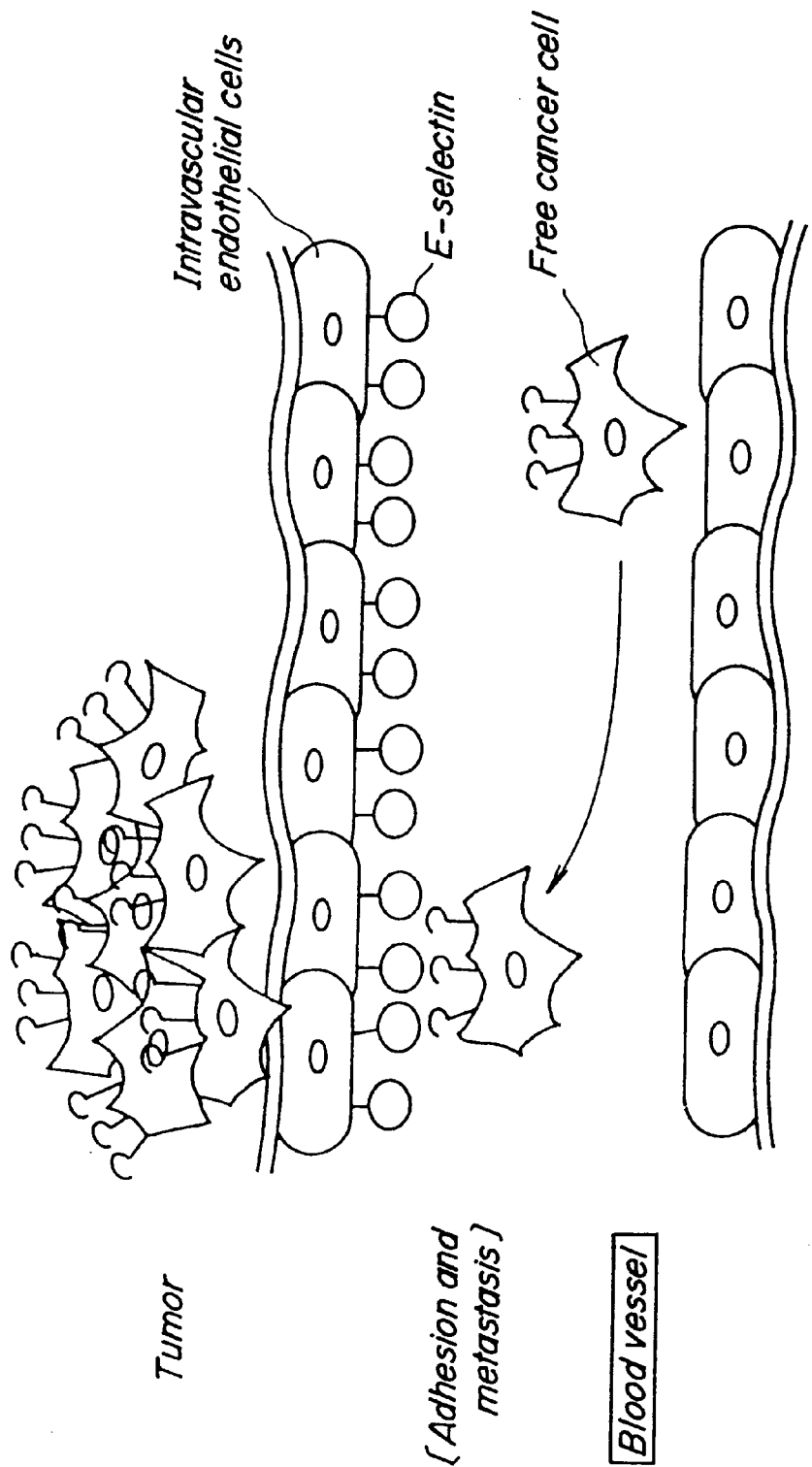
FIG. 1 is a figure for diagrammatically showing the metastasis mechanism of the cancer cells.

FIG. 7 shows E-selection expression appearance in human, wherein FIGS. 7(a), 7(b), 7(c) and 7(d) are microphotographs showing that E-selectin was produced by interleukin 1β in cell-lined intravascular endothelial cell strain #5-1 and human normal intravascular endothelial cells;

FIG. 8 shows inhibition of adhesion between cancer cells and human intravascular endothelial cells, wherein FIGS. 8(a), 8(b) and 8(c) are microphotographs showing an effect that E-selectin is produced by inteleukin 1β and an effect that adhesion of the cancer cells to the intravascular endothelial cells is inhibited by the surface sugar chain of *Streptococcus agalactiae* bacteria Ia type or Ib type; and FIG. 9 shows effect of surface sugar chains from *Streptococcus agalactiae* on cell adhesion bewteen HL-60 cells and human intravascular endothetial cells, wherein FIGS. 9(a) through 9(d) show that the adhesion between the cell-lined intravascular endothelial cell strain #5-1 or human normal intravascular endothelial cell and the cancer cells HL-60 is inhibited by the surface sugar chain of *Streptococcus agalactiae* bacteria Ia type or Ib type.

FIGS. 10(a)–(d) show the effect of surface sugar chains from *Streptococcus agalactiae* on cell adhesion between Colo 201 cells and human intravascular endothelial cells.

BEST MODE FOR PRACTICING THE INVENTION

The sugar chain to be used in the present invention can be obtained by cultivating a strain of the *Streptococcus agalactiae* Ia type or Ib type, fixing the resultant, precipitating a polysaccharide in a given solvent, and then separating and purifying the resulting surface polysaccharide by a gel filtration process or like.

As pharmaceutical preparations in the present invention, oral preparations such as a tablet, a capsule and powder, a percutaneous absorption preparation such as a suppository and a vaginal suppository, and injection preparations such as subcutaneous administration, intraperitoneal administration and intravenous administration may be recited. In the case of preventing the disease, the oral preparations are most preferred, whereas in the case of emergency, the injection preparations are most preferred.

Although the oral preparations, a percutaneous absorption preparation and injection preparations can be formulated according to ordinary processes. The oral preparation and the injection preparation may be recited as follows:

(1) Formulation of an injection preparation: Into 1000 ml of distilled water (pyrogen free) was dissolved 50 g of sialic acid or its polymer, the resulting solution is adjusted to pH 7.0 with a caustic solution, filtered and according to common processes, and aseptically sealed into a 20-ml ampoule as an injection preparation.

(2) Formulation of an oral preparation: A capsule preparation was formed by packing 280 mg of sialic acid or its polymer having passed a 60-mesh sieve into a No. 3 gelatine capsule.

The dosage varies depending upon age, sex, degree of disease, etc. of the patient, and therefore cannot be generally specified. However, an adult may be administrated with 1 to 2000 mg/Kg, preferably 10 to 500 mg/Kg per day when calculated in the form of a sodium salt of sialic acid or its polymer contained in the injection preparation. The number of times of administrations is appropriately 1 to 6, and intravenous drip infusion administration is effective measure.

In the following, the cancer metastasis inhibitor according to the present invention which comprises the surface polysuccharide(s) of the *Streptococcus agalactiae* Ia type and/or Ib type will be explained in more detail with reference to the drawings. (Separation and purification of the surface polysaccharide(s) of *Streptococcus agalactiae* Ia type and/or Ib type)

(1) First, each of the strains of the *Streptococcus agalactiae* Ia type and Ib type are fermented and cultivated for 24 hours in a brain-heart infusion-broth culture, and fixed with a 2 wt % aqueous formalin solution, and a polysaccharide cultivated on the surface of the strain was separated from the strain. The cultivated mixture was subjected to centrifugal separation at 5000 rpm for 20 minutes, and the polysaccharide was precipitated by adding an 80% ethanol aqueous solution to a supernatant thereof. The surface polysaccharide was separated and coarsely purified. Next, the thus obtained polysaccharide was fractioned depending upon the molecular weight by a gel filtration process. A specific polysaccharide was identified according to an ELISA process by using a specific antiserum of the *Streptococcus agalactiae* Ia type or Ib type produced by rabbit.

Figure 3:
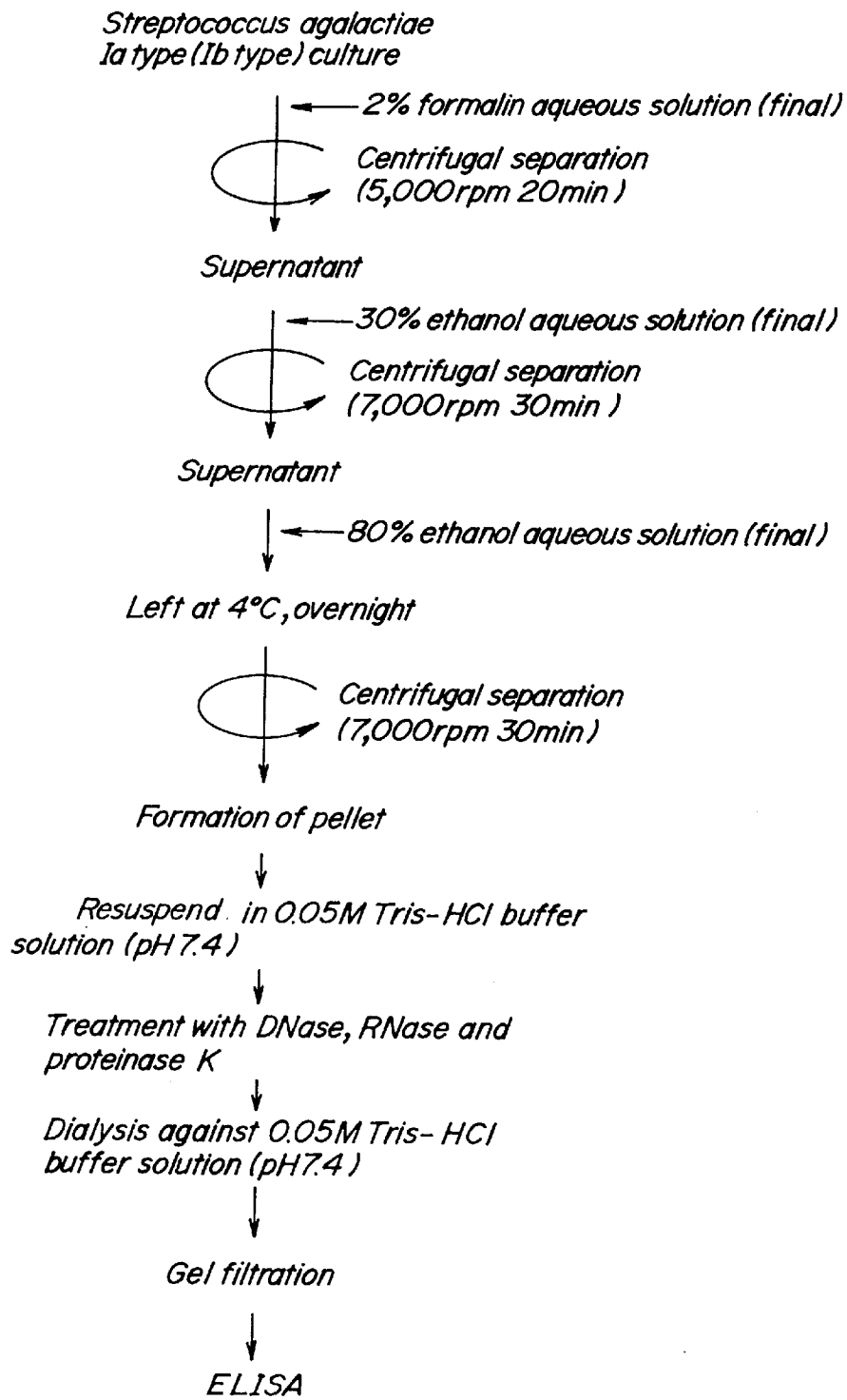
FIG. 3 is a flow chart for illustrating a process for cultivating, purifying and identifying the surface sugar chain of the *Streptococcus agalactia* bacteria Ia or Ib.

(2) Another embodiment of the above process will be shown in more detail by a flow chart in FIG. 3.

Figure 4:
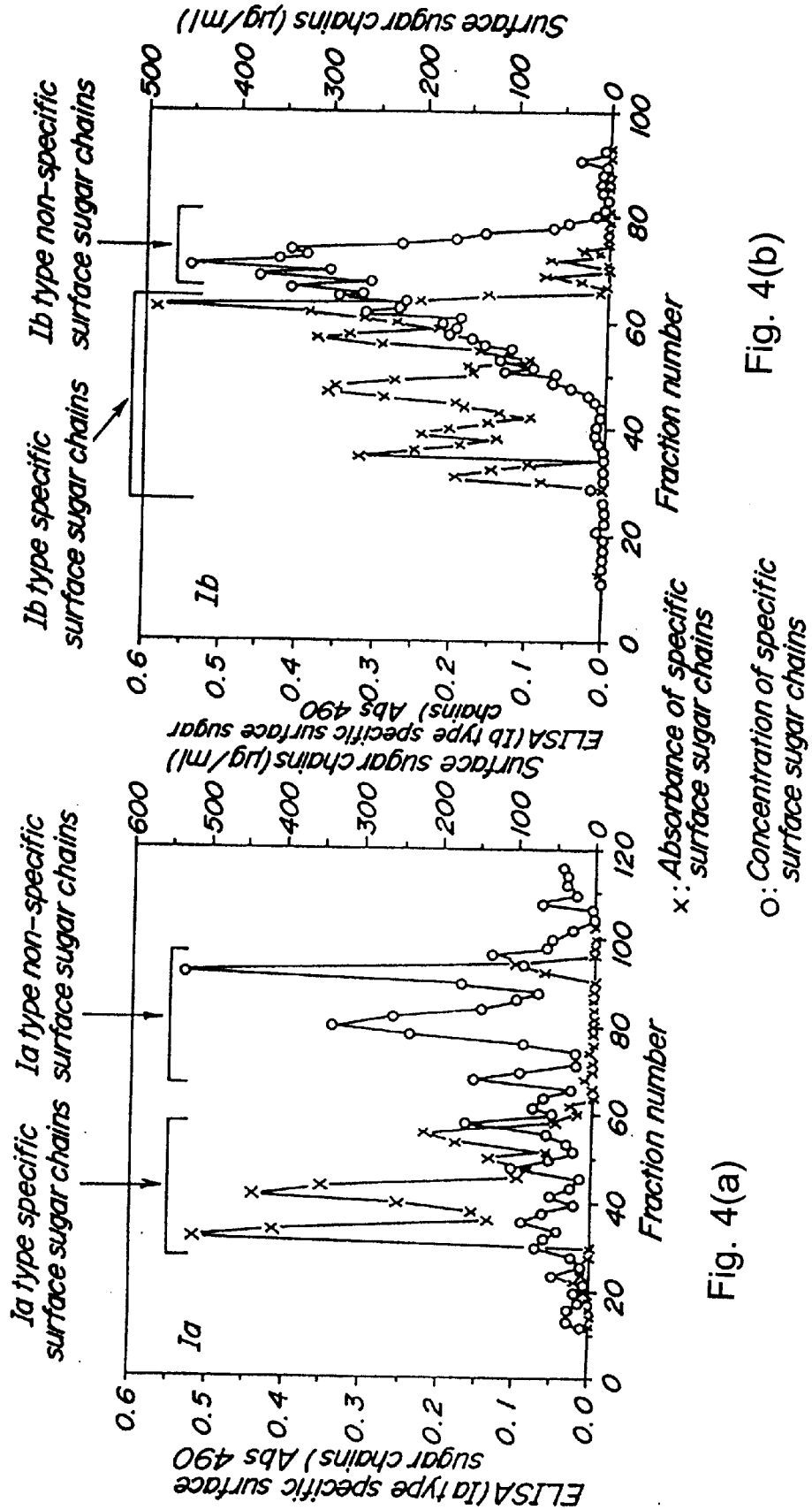
FIG. 4 shows gel filtration profiles of surface sugar chains from *Streptococcus agalactiae,* wherein FIGS. 4(*a*) and 4(*b*) are separation profiles in gel filtration of the sugar chains originating from the surfaces of the *Streptococcus agalactia* bacteria Ia and Ib.

(3) FIGS. 4(a) and 4(b) show fractionating profiles when the surface polysaccharides of the strains of the *Streptococcus agalactiae* Ia type and Ib type were identified by the ELISA process in the gel filtration of their sugar chains, respectively. In each figure, an abscissa gives the fraction number, and an ordinate gives the concentration of the fractionated sugar chain and the absorbance of each fraction at 490 nm ("o" shows the concentration of the sugar chain, and "x" shows the absorbance at 490 nm). In this Example, gel filtration was effected by using Sepharose 4B filled in a column, 1.5 cm in diameter and 90 cm in height. As both a carrier solvent and an eluting liquid, a 50 mM trishydrochloric acid buffer (pH 7.4) was used.

It is seen that with respect to each of the surface polysaccharides of the strains of the *Streptococcus agalactiae* Ia type and Ib, the specific sugar chain was eluted in a larger molecular weight fraction side.

Figure 5:
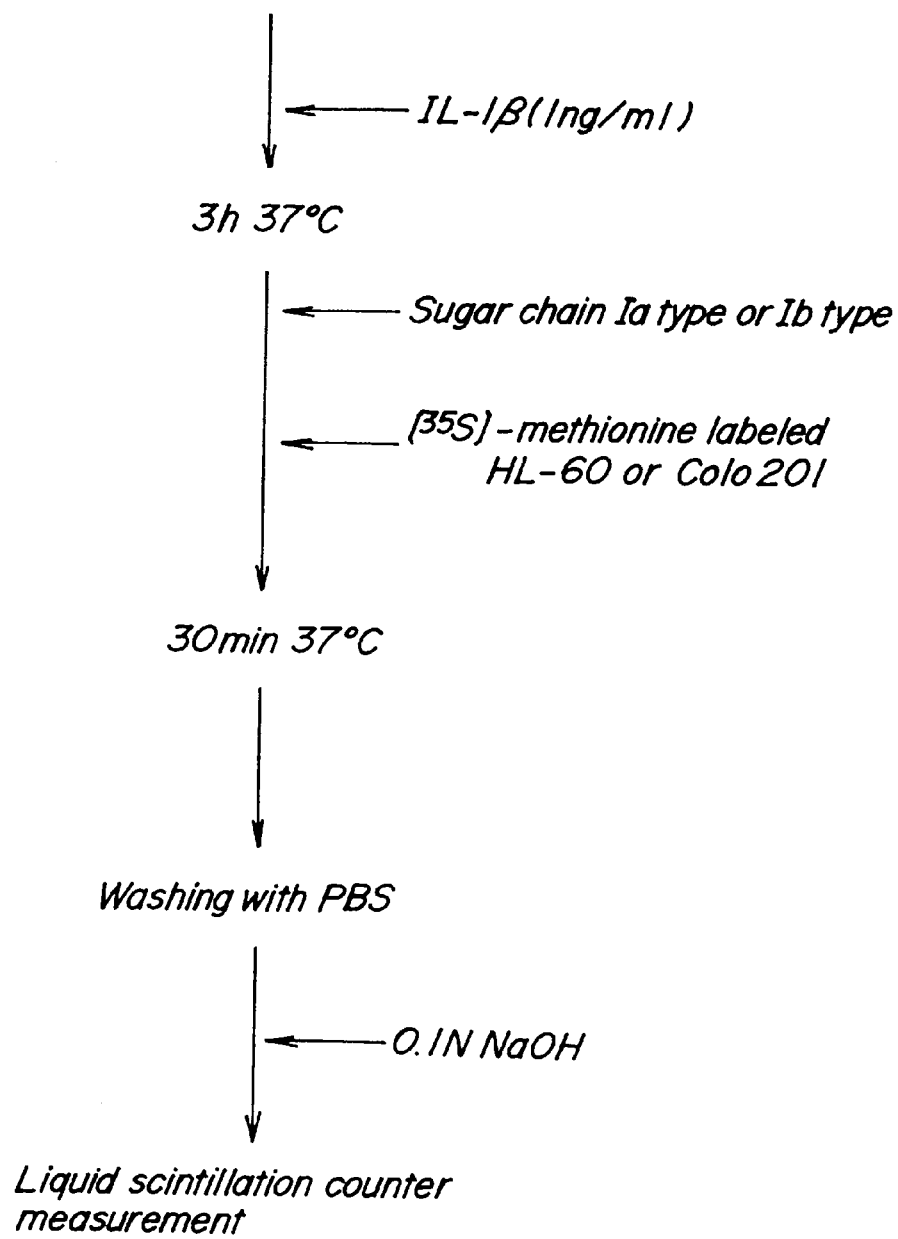
FIG. 5 is a flow chart showing a confirmation test process for adhesion (inhibition)
Figure 6:
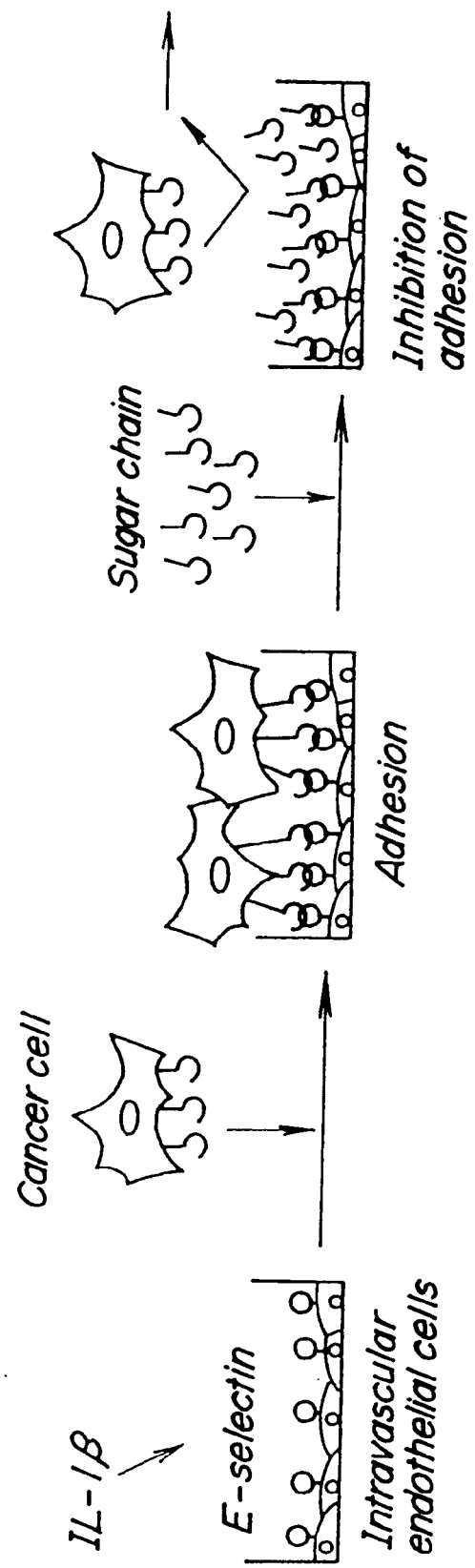
FIG. 6 is a figure for diagrammatically illustrating that the sugar chains originating from the surfaces of the *Strepto-* coccus agalactia bacteria Ia or Ib inhibit the labeled cancer cells from adhering to the intravascular endothelial cells.
Figure 10:
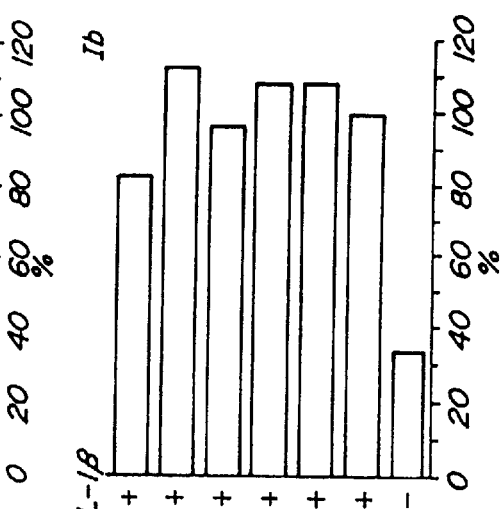
Figure 10C:
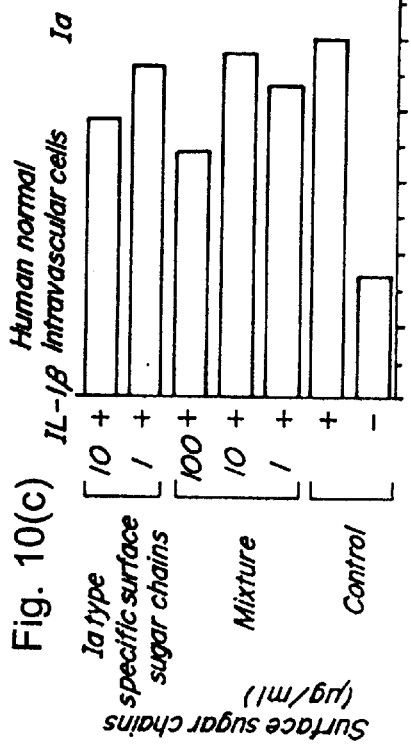
Figure 10D:
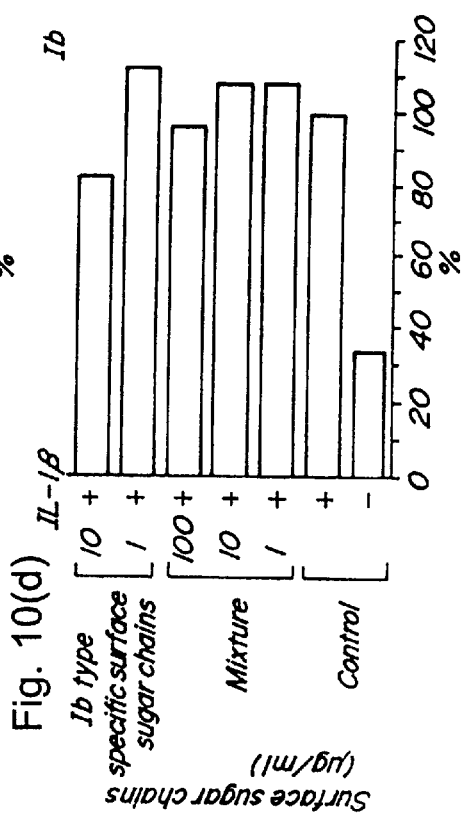
Figure 10A:
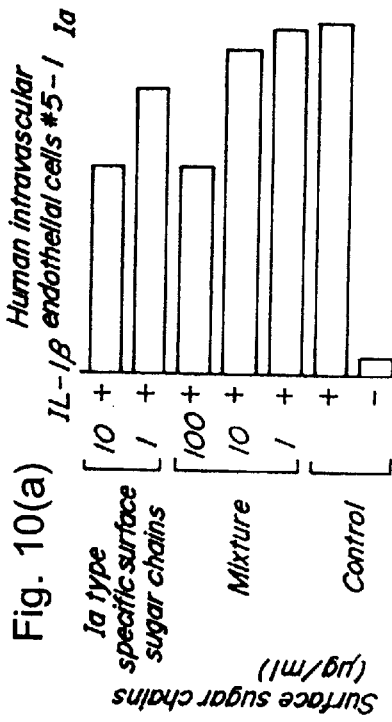
Figure 10B:
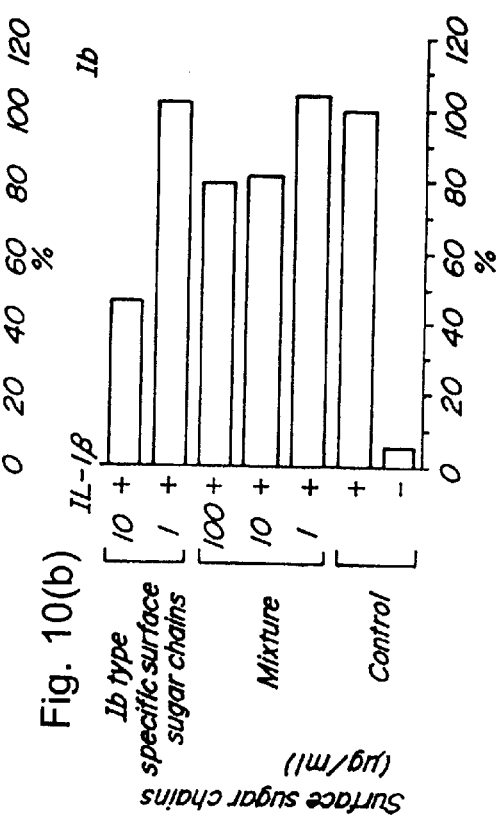

(4) Next, how much adhesion of the cancer cell to the intravascular endothelial cells thus cultivated was inhibited by the addition of the sugar chain obtained above to the intravascular endothelial cells was examined. See FIG. 5. First, intravascular endothelial cells were placed on one plane of a 96-well plate, and appearance of E-selectin was induced by adding interleukin-1β to the cells. The cultivation for about 3 hours made E-selectin appear. The Ia type or Ib type sugar chain was added to it, and $1 \times 10^4$ cancer cells labeled with [$^{35}$S] methionine were added to it, and the mixture was left at 37° C. for 30 minutes as it was. Thereafter, the mixture was immersed in and washed with PBS, and those cancer cells not adhered were washed off. The cells were recovered by adding 100 μl of a 0.1 N aqueous solution of sodium hydroxide to each of the 96-well plates, and a residual radioactivity value was measured by using a liquid scintillation counter. See FIG. 5. FIG. 6 shows that the cells labeled with $^{35}$S methionin are adhered to the intravascular endothelial cells and that such adhesion is inhibited by the above sugar chains.

FIGS. 7(a) through 7(d) are microphotographs obtained by photographing with a fluorescent microscope to confirm whether E-selectin was produced or not at the surfaces of the intravascular endothelial cells, through coloring the human normal intravascular endothelial cells and the cell-lined human intravascular endothelial cell strains #5 with E-selectin antibody. As compared with cases in which no interleukin-1β was added (FIGS. 7(c) and 7(d)), it is clear that appearance of E-selectin was induced in cases where interleukin-1β was added (FIGS. 7(a) and 7(b)).

(6) FIGS. 8(a) through 8(c) are microphotographs showing a state in which the cancer cells are actually adhered to the intravascular endothelial cells. Slender, large cells are intravascular endothelial cells, and whitish, bright, round cells are cancer cells HL-60. As is seen from FIGS. 8(a) to 8(c), as compared with a case where no interleukin-1β was added (FIG. 8a), adhesion of the cancer cells to the intravascular endothelial cells is more conspicuous in a case where interleukin-1β was added (FIG. 8b). In addition, it is seen that when the surface polysaccharide of the strain of the *Streptococcus agalactiae* Ia type or Ib type was further added to the interleukin-1β added case (FIG. 8(c)), the adhesion of the cancer cells to the intravascular endothelial cells are conspicuously inhibited.

(7) FIGS. 9(a) and 9(b) show that the adhesion between the cell-lined intravascular endothelial cell strain #5-1 and the cancer cells HL-60 is inhibited by the surface sugar chain of the strain of the *Streptococcus agalactiae* Ia type or Ib type strain. In FIGS. 9(a) through 9(d), a case where no interleukin-1β was added with no sugar chain is taken as 100%. It is seen that the adhesion of the cancer cells is inhibited by the addition of each of the surface sugar chains of the Ia type and Ib type strains, the sugar chain before the gel filtration (indicated "mixture") and the sugar chain fraction gel filtered and recognized to have the ELISA activity. It is seen that the adhesion of the cancer cells is conspicuously inhibited by 100 μg/ml of the coarsely purified polysaccharide or by 10 μg/ml of the polysaccharide purified through the gel filtration.

In order to confirm that the adhesion of the cancer cells by the sugar chain may not be physically inhibited, the above experimental systems were also observed provided that colominic acid as a polymer of sialic acid was added thereto. As a result, the adhesion inhibiting activity was not almost exhibited by colominic acid as a polysaccharide at such a concentration that the sugar chain originating from the surface of the strain of the *Streptococcus agalactiae* Ia type or Ib type exhibited the adhesion inhibiting activity. Therefore, it was clarified that the inhibition activity exhibited by the sugar chains of the *Streptococcus agalactiae* Ia type and Ib type is attributable to their specific structures.

FIGS. 9(c) and 9(d) give results showing that the adhesion between the human normal intravascular endothelial cells and the cancer cells HL-60 was inhibited by the polysaccharides of the *Streptococcus agalactiae* Ia type and Ib type. It is seen that the same results as those obtained with respect to the cell-lined intravascular endothelial cell strain #5-1 were obtained.

(8) Acute toxicity test

Determination of LD50 in the intraveneous administration with use of Wister series rats (male) revealed that LD50 values of the *Streptococcus agalactiae* Ia type and Ib type were both not less than 2,000 mg/Kg.

We claim:

1. A method for inhibiting metastasis of cancer cells in a patient comprising treating said patient with a metastasis-inhibiting effective amount of a sugar chain separated from the surface of a *Streptococcus agalactiae* of the Ia type or the Ib type.

2. The method of claim 1 wherein said sugar chain is a chain separated from the surface of the *Streptococcus agalactiae* Ia type of the formula:

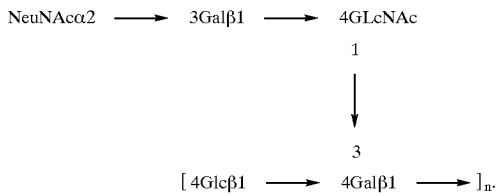

3. The method of claim 1 wherein said sugar chain is a chain separated from the surface of the *Streptococcus agalactiae* Ib type of the formula:

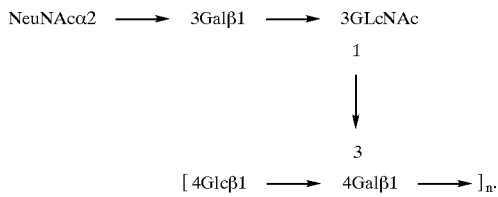

* * * * *